(12) United States Patent
Christopoul

(10) Patent No.: US 11,484,436 B1
(45) Date of Patent: Nov. 1, 2022

(54) PACKAGING OF SEXUAL ACCESSORIES

(71) Applicant: Dean John Christopoul, Boca Raton, FL (US)

(72) Inventor: Dean John Christopoul, Boca Raton, FL (US)

(*) Notice: Subject to any disclaimer, the term of this patent is extended or adjusted under 35 U.S.C. 154(b) by 128 days.

(21) Appl. No.: 17/023,567

(22) Filed: Sep. 17, 2020

Related U.S. Application Data

(60) Provisional application No. 62/902,686, filed on Sep. 19, 2019.

(51) Int. Cl.
 *A61F 6/00* (2006.01)
 *B65D 73/00* (2006.01)
 *B65D 65/18* (2006.01)

(52) U.S. Cl.
 CPC .......... *A61F 6/005* (2013.01); *B65D 73/0057* (2013.01); *B65D 65/18* (2013.01); *B65D 2517/0013* (2013.01)

(58) Field of Classification Search
 CPC ... A61F 6/04; A61F 6/005; B65D 2517/0013; B65D 65/18; B65D 73/0057
 USPC .......................................................... 206/69
 See application file for complete search history.

(56) References Cited

U.S. PATENT DOCUMENTS

| | | |
|---|---|---|
| 5,163,448 A | 11/1992 | Foldesy |
| 5,163,449 A | 11/1992 | van der Valk |
| 5,370,131 A | 12/1994 | Hess |
| 5,425,379 A | 6/1995 | Broad, Jr. |
| 5,715,839 A | 2/1998 | Strauss et al. |
| 6,306,080 B1 | 10/2001 | Mitchell et al. |
| 6,390,095 B1 | 5/2002 | Magnusson |
| 6,453,903 B1 | 9/2002 | Thomas, III |
| 6,454,086 B1 * | 9/2002 | Bryson ............ A61F 6/005 206/209 |
| D496,458 S | 9/2004 | Lin |
| 9,730,829 B1 | 8/2017 | Bublick et al. |
| 2004/0163652 A1 | 8/2004 | Watson |
| 2006/0127441 A1 | 6/2006 | Lomans |
| 2007/0051373 A1 | 3/2007 | Lin |
| 2008/0257361 A1 | 10/2008 | Hakim |

FOREIGN PATENT DOCUMENTS

WO 2018203703 11/2018

OTHER PUBLICATIONS

"Humming Butterfly Vibrating Ring and Condom Combo" found at https://www.amazon.com.
(Continued)

*Primary Examiner* — Anthony D Stashick
*Assistant Examiner* — L Kmet
(74) *Attorney, Agent, or Firm* — John Rizvi; John Rizvi, P.A.—The Patent Professor ®

(57) ABSTRACT

A sexual accessory pack comprising a transparent or translucent sterile ring pack including a penile ring enclosed therein by a releasable film having a pull tab, where the ring pack is removably attached to the outer surface of a condom pack to provide integral packaging of sexual accessories. One or more sexual accessory packs are packaged in an at least partially transparent or translucent retail, such as a transparent or translucent window, to allow purchasers to visually access various characteristics of the packaged penile rings, such as style, shape and size, prior to completing a purchase.

20 Claims, 9 Drawing Sheets

(56) References Cited

OTHER PUBLICATIONS

"Screaming O Condom Disposable Vibrating Ring Condom Pack" found at https://www.amazon.com.
"Durex Elasticity Cock Ring + Durex Condom Close Fit Mini 12pcs" found at https://www.lelong.com.
"Cock Ring Condom, Masturbation Vibrating Ring" found at https://www.alibaba.com.

* cited by examiner

PACKAGING OF SEXUAL ACCESSORIES

CROSS-REFERENCE TO RELATED APPLICATIONS

This application claims the benefit of U.S. Provisional Patent Application Ser. No. 62/902,686, filed on Sep. 19, 2019, which is incorporated by reference herein in its entirety.

FIELD OF THE INVENTION

The present invention relates generally to packages or packaging arrangements, and more particularly, to a sexual accessory pack including a penile ring that is packaged within a ring pack removably attached to the outer surface of a condom pack, where a plurality of sexual accessory packs are packaged for display in retail sales.

BACKGROUND OF THE INVENTION

Many sexual therapists agree that a healthy sexual life helps nurtures both the physical and emotional attributes of males and females. Medical studies have demonstrated the benefits of having a healthy sex life including factors such as relieving stress and tension, promoting better sleep, increasing self-esteem, and generally providing a positive outlook on a couple's relationship. One sexual accessory that is often used during the course of sexual activity is a male or female condom that is used to not only prevent unplanned or unwanted pregnancies, but also to protect individual participants from sexually transmitted diseases. Condoms are typically manufactured from a thin, latex material, or alternatively from a polyurethane or polyisoprene for individuals who are allergic to latex. Condoms are generally sealed in individual packs and disposed in retail packages for sales and distribution. Each condom pack generally includes a square geometric shape with a company logo typically presented on the outer surface of the condom pack. Individuals often visit their local pharmacy or retail store to purchase a box of condom packs that include condoms of various sizes, construction, and styles.

Another sexual accessory that is also employed by male individuals during sexual activity is a penile ring which is often referred to as a C-ring, or a cock ring. The penile ring is a circular ring that is placed around the shaft of the penis, typically at the base, to help retain an erection by trapping or preventing blood from leaving the penis, adding girth, and prolonging ejaculation during intercourse. Men who suffer from erectile dysfunction (ED) often use penile rings to maintain an erection during sexual activity. Although penile rings provide some recourse for males suffering from erectile dysfunction, penile rings also provide a versatile toy that is used to sexually stimulate various anatomical regions of sexual partners enhancing their sexual pleasure and intimacy. Penile rings come in a variety of different models, shapes and sizes, and are generally constructed from rubber, silicone, nylon, neoprene, or from a rigid material such as metal or glass. Some penile rings include a smooth, outer surface, while other penile rings include protrusions or nubs formed on the outer surface to enhance frictional contact between the ring and anatomical regions of the sexual partner during use. Penile rings are sold individually in loose form, as well as packaged and sold in various quantities.

It is not uncommon for men to employ the use of sexual accessories involving both a condom and a penile ring when engaging in intimate sexual activity with a partner or partners. Individuals use the condoms to prevent pregnancies and/or to protect themselves from sexually transmitted diseases, while employing a penile ring to manage an erection, and/or stimulate various regions to enhance sexual pleasure of their partner or partners. When acquiring sexual accessories, individuals typically have to purchase a condom separately from a penile ring as two separate products. While both items, a condom and a penile ring, may sometimes be available and purchased from the same location, such as in specifically designated sex shops or over the internet, each product is still packaged and sold separate from one another. For example, individuals purchase condoms at a local pharmacy or retail store, but must purchase penile rings from other locations or from other sources thus obligating individuals to often make separates purchases from two distinct sellers. Although some manufactures have developed packaging for combining various sexual items such as supplying batteries and/or lubrication with sexual appliances, or packaging lubrication packs with condoms, none have provided a package arrangement that combines both a condom and penile ring where distinct characteristics of the penile ring are visually presented to possible buyers before purchase. Some manufacturers have incorporated penile rings directly within the body of the condom itself as one integral unit. This approach however, forces individuals to utilize both sexual accessories with no option to select one over the other, nor does it permit buyers to see the style, shape or size of penile ring before purchase is made. Although condoms are often a one-size fits all, the same cannot be said for penile rings. Penile rings are generally resilient and stretch, however, such stretching capacities have limitations, and thus, individuals must often consider size when purchasing penile rings. In practice, penile rings are either conventionally sold in opaque packaging that prevents buyers from viewing characteristics such as style, shape, and size, are sold as a loose item, or are sold in a single size. Such conventional packaging arrangements still require the separate purchase of a condom and a penile ring.

Accordingly, there exists a need to solve at least one of the aforementioned problems mentioned herein.

SUMMARY OF THE INVENTION

The present invention is directed to a sexual accessory pack which may include a penile ring packaged within a sterile ring pack having a quick release pull tab, wherein the ring pack is removably attached to the outer surface of a condom pack to provide an integral accessory pack, and wherein a plurality of sexual accessory packs are packaged in a transparent or translucent package, or a cardboard box including a transparent or translucent window, to permit buyers to visually inspect certain characteristics such as style, shape and size of penile rings when contemplating a purchase.

In a first embodiment, the present invention provides a sexual accessory package for display in and sale from a retail shopping establishment, the package comprising: a condom pack having an outer surface surrounding an inner enclosure, the inner enclosure including a condom removably enclosed therein; a penile ring pack including a circular body having a planar front panel integral with a circular wall having an open end disposed opposite the planar front panel, the open end at least partially defined by a perimeter therearound, wherein the planar front panel and the circular wall cooperatively form a ring chamber therebetween; a penile ring disposed in the ring chamber of the penile ring pack; a release film overlying the open end of the circular wall opposite the planar front panel and removably attached to at least the perimeter of the circular wall, thereby removably enclosing the penile ring in the ring chamber of the penile ring pack; and the penile ring pack removably attached to the outer surface of the condom pack such that the planar front panel of the penile ring pack is disposed opposite the outer surface of the condom pack for display in the retail shopping establishment to facilitate viewing and sale of the package comprising both the condom and the penile ring.

In one aspect, the planar front panel, or the circular wall, or both, comprise a transparent material to permit visual access to the packaged penile ring.

In another aspect, the circular wall includes a predetermined height that defines the depth of the ring chamber, and a diameter that is slightly larger than the diameter of the penile ring.

In another aspect, the diameter of the penile ring and circular wall includes a plurality of different diameters that define a small size, a medium size, and a larger size.

In another aspect, the release film includes a pressure-sensitive adhesive.

In another aspect, the pull-tab includes a triangular shape. The pull-tab may also include a stiffener that is applied to one or both outer surfaces of the pull-tab.

In another aspect, the pull-tab includes a second pull-tab for removing the penile ring pack from the outer surface of the condom pack.

In another aspect, the pull-tab is pulled towards the planar, front panel to remove the ring pack from the outer surface of the condom pack, and away from the planar, front panel to remove the release film from the ring pack to expose and allow access to the packaged penile ring.

In another aspect, the perimeter includes a planar top edge to removably attach the release film thereto.

In yet another aspect, the retail package comprises a transparent package having an outwardly extending window forming a chamber for packaging one or more sexual accessory packages therein, where the retail package includes an opening.

In yet another aspect, the retail package comprises a transparent package having an outwardly extending portion forming a chamber for packaging one or more sexual accessory packages therein, where the retail package includes a hanger opening, and where a first sexual accessory package is attached to a second sexual accessory package, via, a perforated tear line, such that two sexual accessory packages are displayed within the outwardly extending window one on top of the other.

In another aspect, the retail package comprises a panel having a front and back, a border including a surrounding wall attached to the front to define a storage chamber, and including a window frame and transparent window affixed to the inner surface of the window frame, where one or more sexual accessory packages are stored within the storage chamber and accessibly viewable through the transparent window. The retail package is constructed from a cardboard or rigid paper material, and includes a hanger opening.

In another aspect, one or more retail packages are disposed on one or more hangers on a display rack.

These and other objects, features, and advantages of the present invention will become more readily apparent from the attached drawings and the detailed description of the preferred embodiments, which follow.

BRIEF DESCRIPTION OF THE DRAWINGS

The embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

Figure 1:
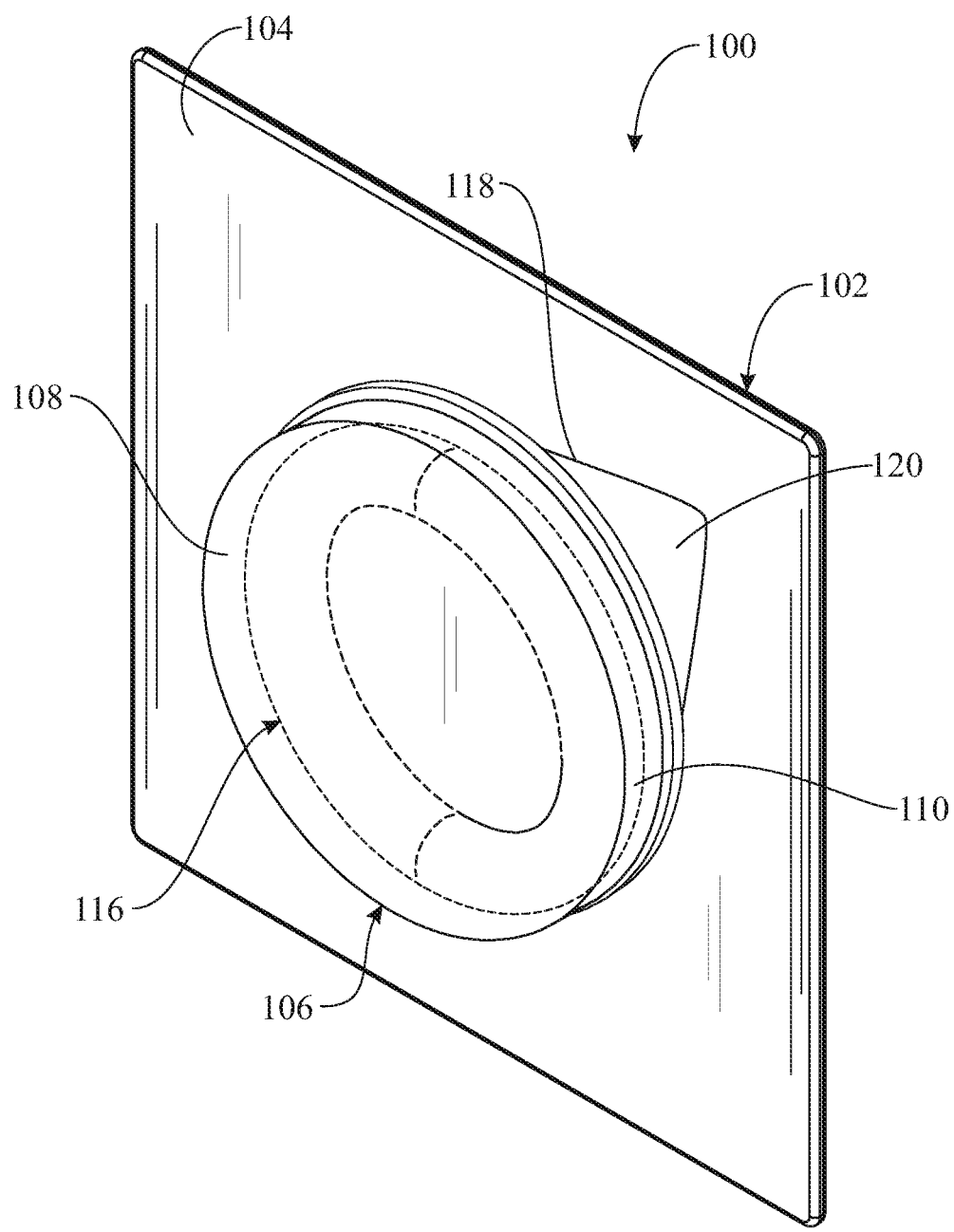
FIG. 1 presents a front perspective view of a sexual accessory package, showing a ring pack including an enclosed penile ring, and a pull-tab, where the ring pack is removably attached to the outer surface of a condom pack, in accordance with one embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed to a sexual accessory pack comprising a transparent, sterile ring pack including a penile ring enclosed therein by a releasable film having a pull tab, where the ring pack is removably attached to the outer surface of a condom pack to provide an integral package for sexual accessories. A single or multiple sexual accessory packs are packaged in a transparent package, or a cardboard box including a transparent window, to provide accessible viewing of the penile rings when contemplating style, shape, and size during purchase. In at least one embodiment, a sexual accessory package for display in and sale from a retail shopping establishment, the package comprising: a condom pack having an outer surface surrounding an inner enclosure, the inner enclosure including a condom removably enclosed therein; a penile ring pack including a circular body having a planar front panel integral with a circular wall having an open end disposed opposite the planar front panel, the open end at least partially defined by a perimeter therearound, wherein the planar front panel and the circular wall cooperatively form a ring chamber therebetween; a penile ring disposed in the ring chamber of the penile ring pack; a release film overlying the open end of the circular wall opposite the planar front panel and removably attached to at least the perimeter of the circular wall, thereby removably enclosing the penile ring in the ring chamber of the penile ring pack; and the penile ring pack removably attached to the outer surface of the condom pack such that the planar front panel of the penile ring pack is disposed opposite the outer surface of the condom pack for display in the retail shopping establishment to facilitate viewing and sale of the package comprising both the condom and the penile ring.

Figure 2:
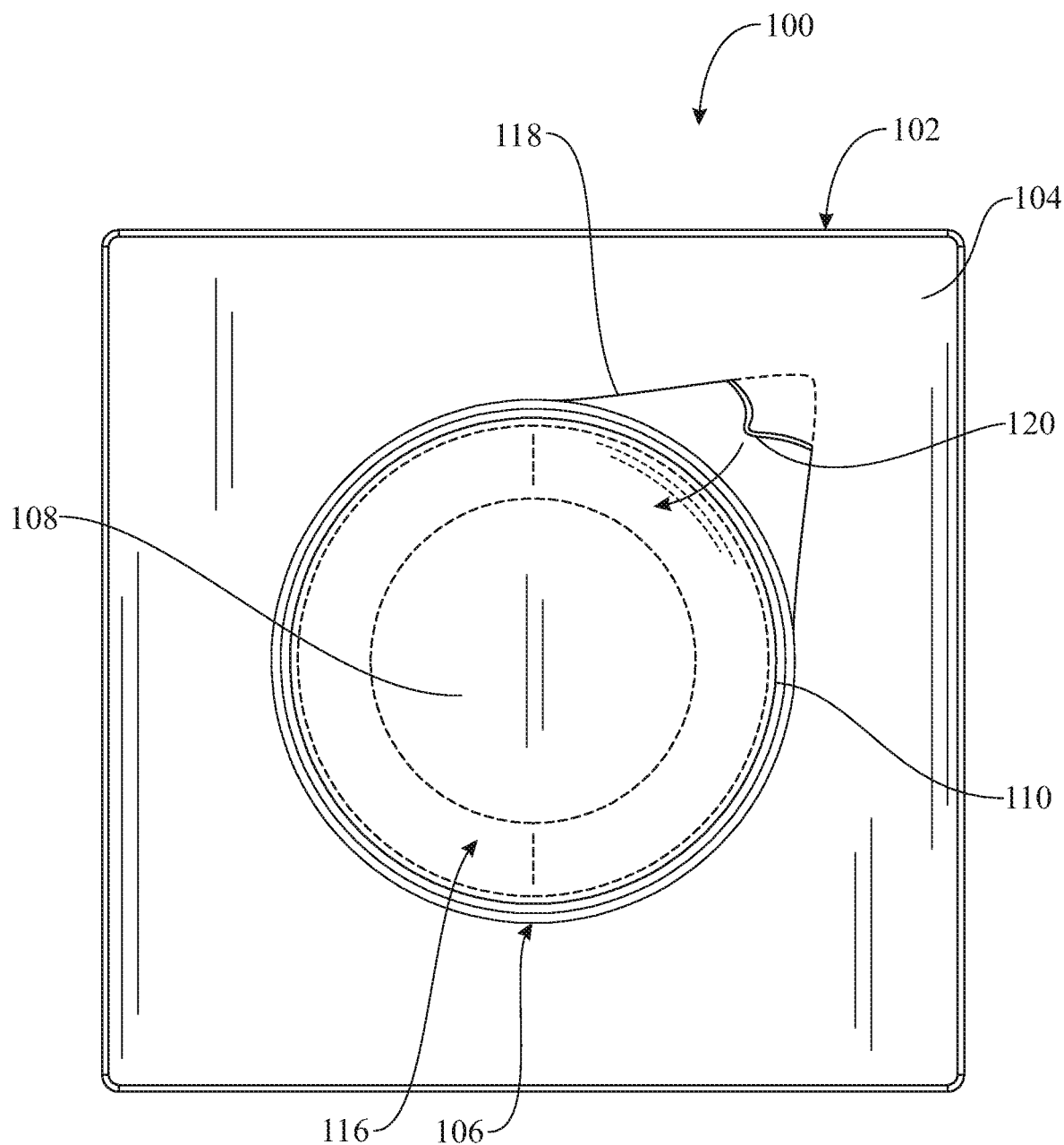
FIG. 2 presents a front view of the sexual accessory package of FIG. 1, showing a portion of the pull tab partially released from the outer surface of the condom pack to readily remove the ring pack from the condom pack for accessing the penile ring.

Referring now to FIGS. 1 and 2, there are shown a front perspective view and a front view, respectively, of a sexual accessory package 100, in accordance with one embodiment of the present invention. The sexual accessory package 100 includes a condom pack 102 that generally comprises any well-known condom pack available for sale on the market by retailers in designated brick and mortar retail stores, or over the internet. The condom pack 102 generally comprises a package having a sealable cavity or inner enclosure for housing a rolled condom therein where the sealable cavity being sealed using well-known mechanical processes and techniques. The condom is typically constructed from a thin, latex material, or alternatively from a polyurethane or polyisoprene material for individuals who are allergic to latex. A great majority of condom packs 102 are constructed from a thin, plastic or foil packaging material that permits users to easily tear a portion of the condom pack 102 by hand to access the condom therein. The condom pack 102 may comprise any dimensional size and geometric shape but for the most part such condom packs 102 generally comprise a square configuration. For illustrative purposes only, it is understood that reference made to the term, "condom" or "condom pack" herein may include a condom that is specifically designed for males or females.

Figure 4:
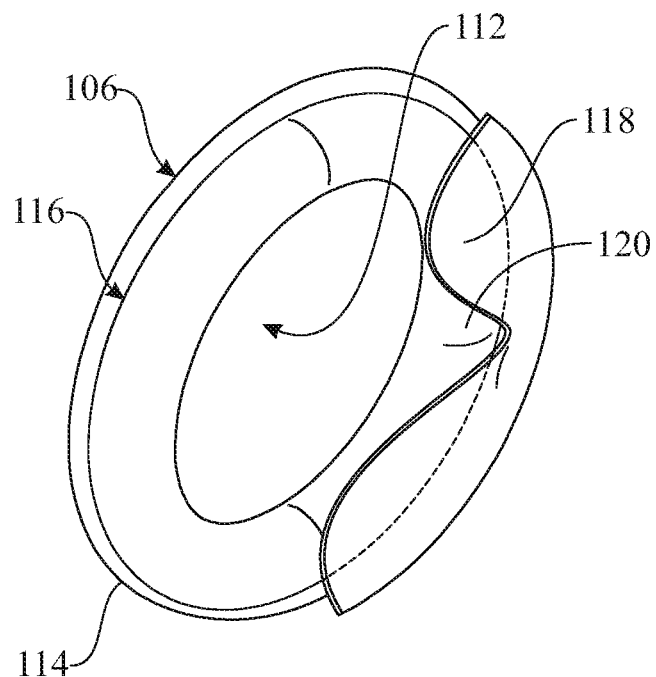
FIG. 4 presents a back perspective view of the ring pack of FIG. 3, showing the releasable film partially peeled away from the ring pack to accessibly expose the penile ring.

The sexual accessory pack 100 further includes a penile ring pack 106 having a planar front panel 108 integral with a circular wall 110 that define a ring chamber 112, the circular wall 110 having an open end opposite the planar front panel 108 and having a circular peripheral edge or perimeter 114, as better illustrated in FIG. 4. The sexual accessory pack 100 is removably attached to the outer surface 104 of the condom pack 102 using any well-known material such as two-face tape, pressure-sensitive adhesive, or glue. The defined ring chamber 112 is designed to store one or more penile rings 116 therein. The diameter and height of the circular wall 110 is selected to accommodate penile rings 116 of different diameters corresponding to male individuals having penises of different girth sizes, as well as to accommodate packaging a quantity of penile rings 116 therein as well. Thus, the height of the circular wall 110 may be greater to increase the depth of the ring chamber 112 for packaging multiple penile rings 116 therein in a stacked configuration. It will be understood that the circular wall 110 may also comprise a stepped wall configuration to provide a series of varied diameters in which penile rings 116 of different sizes can be enclosed one on top of the other within the ring chamber 112 is a size varying arrangement.

The penile ring 116, or each of a plurality of penile rings 116, comprise any commonly well-known penile ring 116 sold over in brick and mortar retail stores or over the internet and includes any style, shape, and diametrical size. The penile ring or rings 116 may include either a smooth outer surface, or an outer surface including any number of protrusions, nubs, bulbs, or ridges, include vibrating, sounding or lighting elements, and may comprise any style, design, shape, color, or pattern. The penile ring or rings 116 may be constructed from silicone, polymer, plastic, rubber, metal, wood, ceramic, or glass. In one embodiment, penile ring 116 may be characterized as being small, medium, or large in size to accommodate males having penis girths of different sizes.

In at least some embodiments, either the planar front panel 108, or the planar front panel 108 and the surrounding circular wall 110, are constructed from a transparent, semi-transparent, translucent, or semi-translucent material, so as to provide quick, accessible viewing of the enclosed penile ring or rings 116 by potential buyers. However, it is appreciated that there may be particular situations or circumstances that would require either or both of the planar front panel 108, and/or the surrounding circular wall 110 to comprise an opaque material to restrict visibility of the packaged penile ring 116. Exemplary materials that can be used to construct the penile ring pack 106 may include, but are not limited to, polyethylene terephthalate (PETE), polypropylene, or synthetic or non-synthetic polymers, or other plastics commonly used in packaging, foil, cardboard, paper, reinforced cardboard or paper, or any combination thereof. A penile ring pack 106 may be constructed using any well-known processes or techniques including for example, vacuum packaging, press packaging, molding, stamping, or other methods.

The penile ring pack 106 further includes a release film 118 provided on the back of the penile ring pack 106 for covering and securely enclosing the penile ring 116 within the ring chamber 112, until such time it is removed for use. The release film 118 is removably attached to the outer circular perimeter 114 of the circular wall 110 such as via a pressure-sensitive adhesive, glue, permanent adhesive, or silicone glue. In one embodiment, the circular perimeter 114 may include a planar lip having a predetermined width to provide a greater surface area for securely attaching the release film 118. The release film 118 may comprise a generally square shape that is wider than the diameter of the circular perimeter 114 or, alternatively, the release film 118 may comprise a generally round configuration that is equal or larger than the diameter of the circular wall 110. It is to be appreciated that the release film 118 may include a single-ply or a multi-ply sheet having a predetermined thickness, flexibility, rigidity, and/or texture.

In at least one embodiment, the release film 118 includes a pull-tab 120 that is either separately attached to, or integral with, the release film 118. In one exemplary embodiment, the pull-tab 120 comprises a generally triangular shape but other shapes and sizes may be implemented for all intended purposes. The pull-tab 120 is designed to permit users to easily grasp or pinch the corner of the pull-tab 120 using a thumb and index finger of one hand, and simply pull the tab 120 to completely remove the penile ring pack 106 from the outer surface 104 of the condom pack 102, as denoted by the directional arrow shown in FIG. 2. It is to be appreciated that the penile ring pack 106 may include two pull tabs 1210 wherein one pull-tab 120 is used to remove the penile ring pack 106 from the outer surface 104 of the condom pack 102, and the other pull-tab 120 is used for peeling the release film 118 from the back of the penile ring pack 106. A pull-tab 120 in accordance with the present invention may include a stiffening material, or a stiffener, such as cardboard, or stiff paper that is attached to at least a portion of the pull-tab 120 to provide rigidity, and durability, particularly when maneuvering the pull-tab 120 during use.

Figure 3:
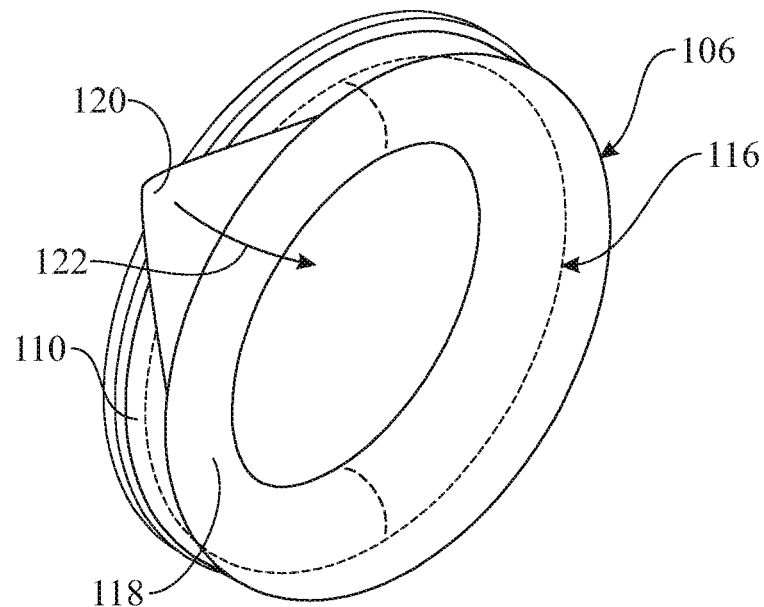
FIG. 3 presents a back perspective view of the ring pack of FIG. 1 completely detached from the condom pack, and including the enclosed penile ring, and the pull-tab, showing a directional arrow for pulling the pull-tab to peel a releasable film from the ring pack to gain access to the packaged penile ring.

Turning to FIGS. 3 and 4, there are shown back perspective views of the penile ring pack 106 shown completely removed from the outer surface 104 of the condom pack 102. The release film 118 securely covers and retains the penile ring 116 within the ring chamber 114. Users gain access to the penile ring 116 by grasping the pull-tab 120 with the index finger and thumb of one hand and pulling the release film 118 away from the back of the penile ring pack 106 in the direction noted by the directional arrow 122. As shown in FIG. 4, in circumstances wherein a pressure-sensitive adhesive is use in attaching the release film 118 to the perimeter 114 of the chamber 112, users can simply and easily peel the release film 118 from the back of the penal ring pack 106 to expose the enclosed penile ring 116. It will be understood that a pull-tab 120 in accordance with the present invention may be pulled by individuals in two separate and distinct directions. As one example, in FIG. 2 the pull-tab 120 is pulled away from the outer surface 104 of the condom pack 102 in the direction of the directional arrow thereon and towards the planar front panel 108 to remove the ring pack 106 from the condom pack 102, and then, the pull-tab 120 is pulled outwards and away from the planar front panel 108 in the direction of arrow 122 to remove the release film 118 from the penile ring pack 106 to gain access to the penile ring 116 for use. As such, a pull-tab 120 in accordance with at least one embodiment of the present invention may be multi-functional.

It will be appreciated that in at least one alternative embodiment, a perimeter 114 or circular wall 110 of a penile ring pack 106 may comprises an integral hinge (not shown) that permanently attaches to the outer surface 104 of the condom pack 102 for permanently retaining the penile ring pack 106 to the condom pack 102 via, the hinge. For example, users may partially detach and swing the penile ring pack 106 away from the outer surface 104 of the condom pack 102, via the hinge, remove the release film 118 in back of the penile ring pack 106, via, the pull-tab 120, and access the penile ring 106, where the penile ring pack 106 remains affixed to the condom pack 102 via, the hinge, during the process. This feature eliminates the need of having to locate and discard an empty condom pack 102 and an empty penile ring pack 106 separately after use. In yet another embodiment, the penal ring pack 106 may be integrally formed and constructed as one unit with the condom pack 102 in which the planar front panel 108, or a portion of the circular wall 110, or both, include a perforated tear line for removing a portion of or all of the planar front panel 108, and/or all or a portion of the circular wall 110 to gain access to the penile ring 116 enclosed within the ring chamber 112.

Figure 5:
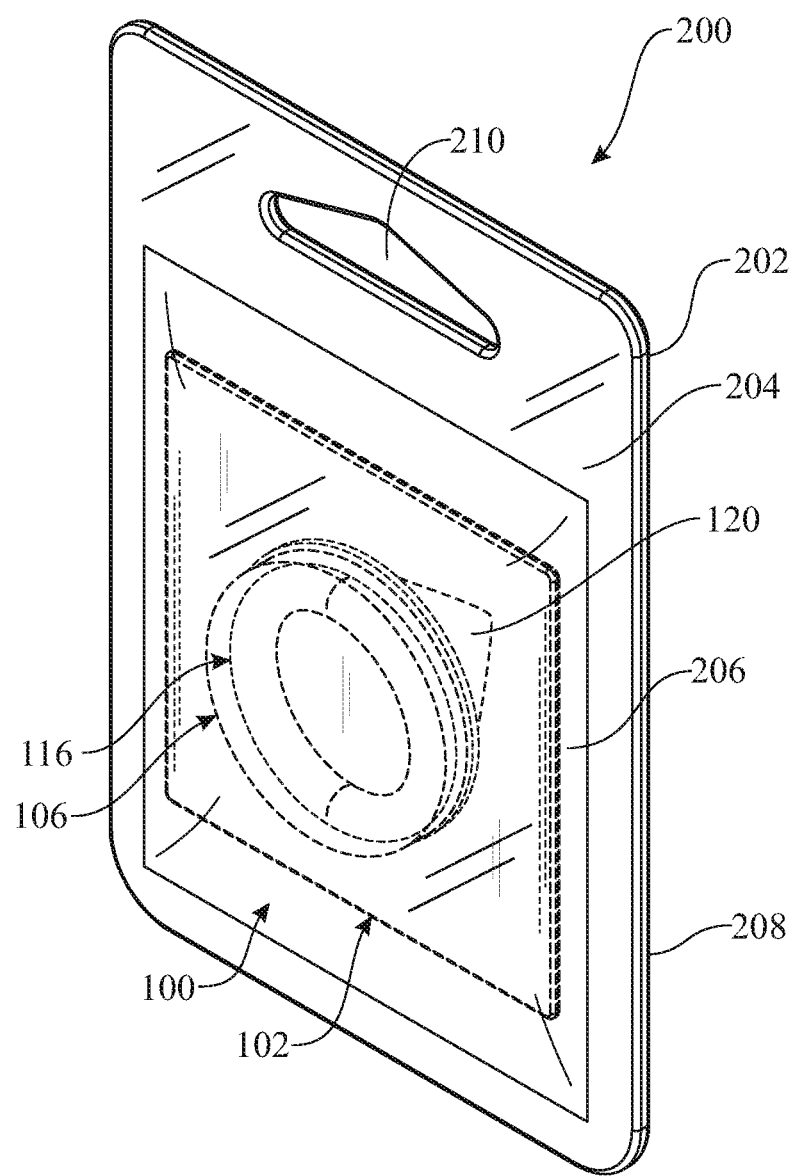
FIG. 5 presents a front perspective view of a transparent retail package including a sexual accessory package of FIG. 1 enclosed within the retail package for readily displaying and selling the sexual accessory package in a retail store.
Figure 6:
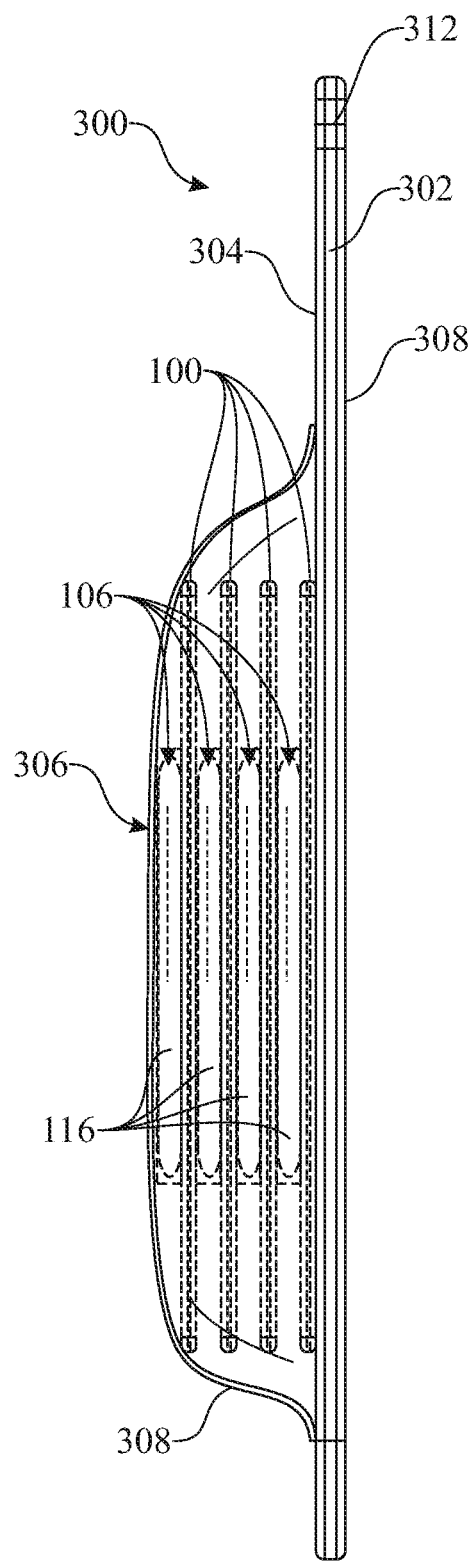
FIG. 6 presents a side view of a transparent retail package including a plurality of sexual accessory packages of FIG. 1, enclosed within the retail package for readily displaying and selling the sexual accessory packages in a retail store.

Turning now to FIG. 5, there is shown a front perspective view of a transparent or translucent retail package 200 for packaging and displaying a sexual accessory package 100 for retail display and sale. The transparent retail package 200 includes a rigid panel 202 having a front panel 204 including an outward extending portion 206, and a back panel 208 that form a storage cavity for packaging a sexual accessory package 100 therein. In one embodiment, both the outward extending portion 206 and back panel 208, respectively, are each constructed from a transparent or translucent plastic material. Alternatively, only the outward extending portion 206 is transparent or translucent while the back panel 208 comprises an opaque cardboard backing. The transparent, outward extending portion 206 provides the added convenience of viewing the penile ring 116 through the transparent planar front panel 108 of the penile ring pack 106 to ascertain the physical characteristic of the package penile ring 116 such as style, shape, and size. The ability to visually inspect the penile ring 116 allows purchasers to make a quick, easy and more informed decision when shopping for penile rings 116. The transparent retail package 200 includes a hanger opening 210 for hanging the transparent retail package 200 on a display rack in a retail store.

Another transparent or translucent retail package 300 is provided for packaging and displaying a plurality of sexual accessory packages 100 in a single retail package 300 for retail display and sale. The transparent or translucent retail package 300 includes a rigid panel 302 having a front panel 304 including an outward extending portion 306 to provide a greater storage cavity for packaging more sexual accessory packages 100 therein, and a back panel 308. The outward extending portion 306 and back panel 308, respectively, are each constructed from a transparent or translucent plastic material. As before, alternatively, the outward extending portion 306 is constructed of a transparent or translucent material, while the back panel 308 comprises an opaque cardboard backing. The transparent or translucent outward extending portion 306 once again provides the added convenience of viewing the transparent penile ring packs 106 to ascertain the physical characteristic of the packaged penile ring 116 such as style, shape, and size, to aid a customer in selecting and purchasing the packaged penile ring 116.

Figure 7:
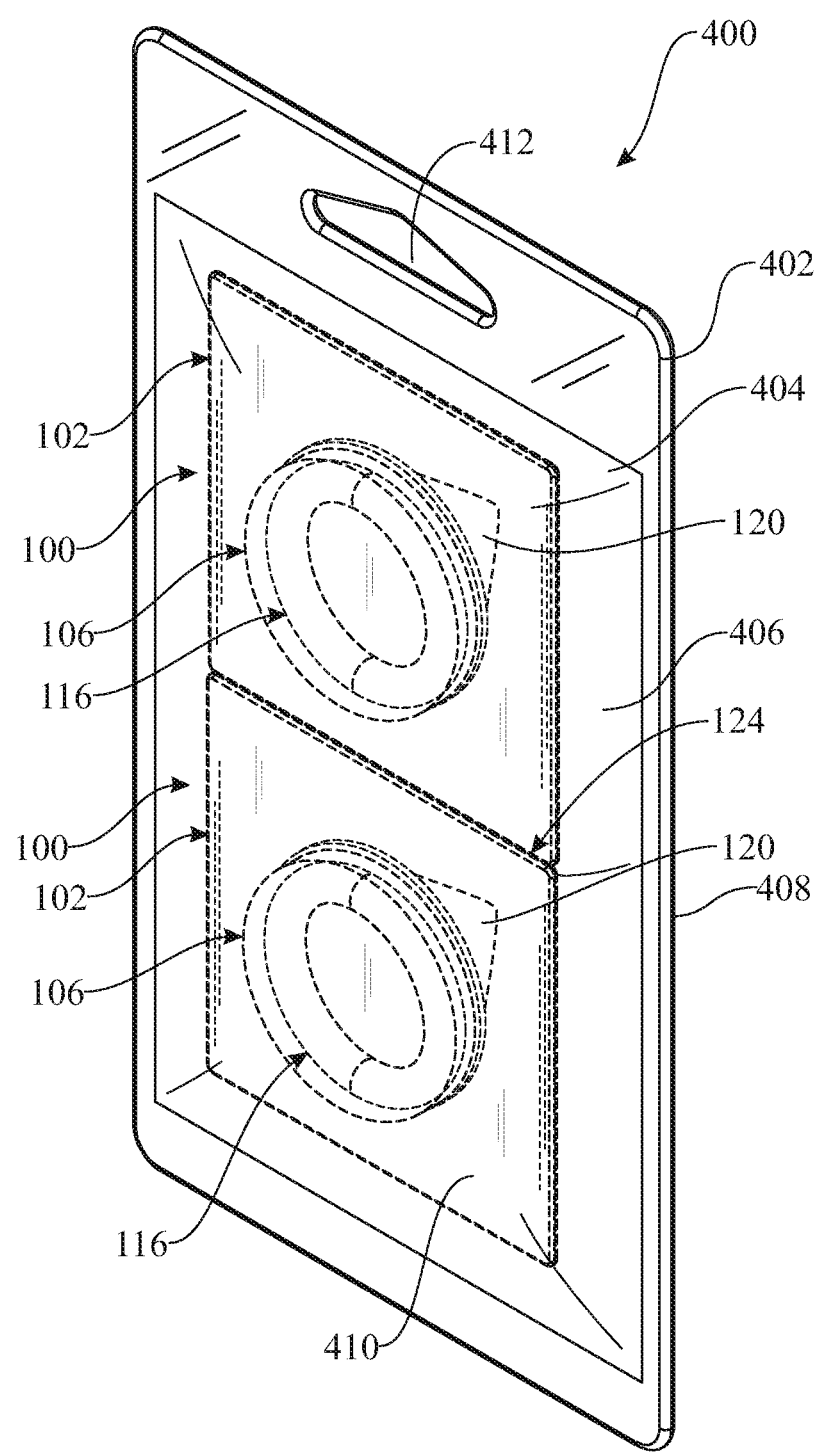
FIG. 7 presents a front perspective view of another transparent retail package including a plurality of sexual accessory packages attached together via, a perforated tear line, and enclosed within the retail package for readily displaying and selling the sexual accessory packages in a retail store.

Turning now to FIG. 7, there is shown a front perspective view of a transparent or translucent retail package 400 for packaging and displaying a plurality of sexual accessory packages 100 in a single retail package 400 for retail display and sales, in accordance with an alternative embodiment of the present invention. The transparent or translucent retail package 400 includes a rigid panel 402 having a longer length than that of retail package 200 in FIG. 5. The retail package 400 includes a front 404 panel having an outward extending portion 406 that provides a storage cavity for packaging at least two sexual accessory packages 100 therein, and a back panel 408. In at least one embodiment, such as is shown in the illustrative embodiment of FIG. 7, a first sexual accessory package 100 is attached to a second sexual accessory package 100 via a perforated tear line 124 preventing one package from sliding or moving behind the other in the storage cavity of the retail package 400. The outward extending portion 406 and back panel 408 are constructed from a transparent or translucent plastic material. Also as before, alternatively, the outward extending portion 406 is transparent or translucent while the back panel 408 comprises an opaque cardboard backing. The transparent or translucent outward extending portion 406 allows purchasers to view the transparent penile ring packs 106 to ascertain the physical characteristic of the package penile ring 116 such as style, shape, and size. In this embodiment, a first sexual accessory pack 100 may include a penile ring 116 having one size, and a second sexual accessory pack 100 having a penile ring 116 of another size, both packaged together within the transparent retail package 400 and attached together via the perforated tear line 124. As with the other packages 200, 300, retail package 400 includes an opening 412 for mounting on a rack for retail display.

Figure 8:
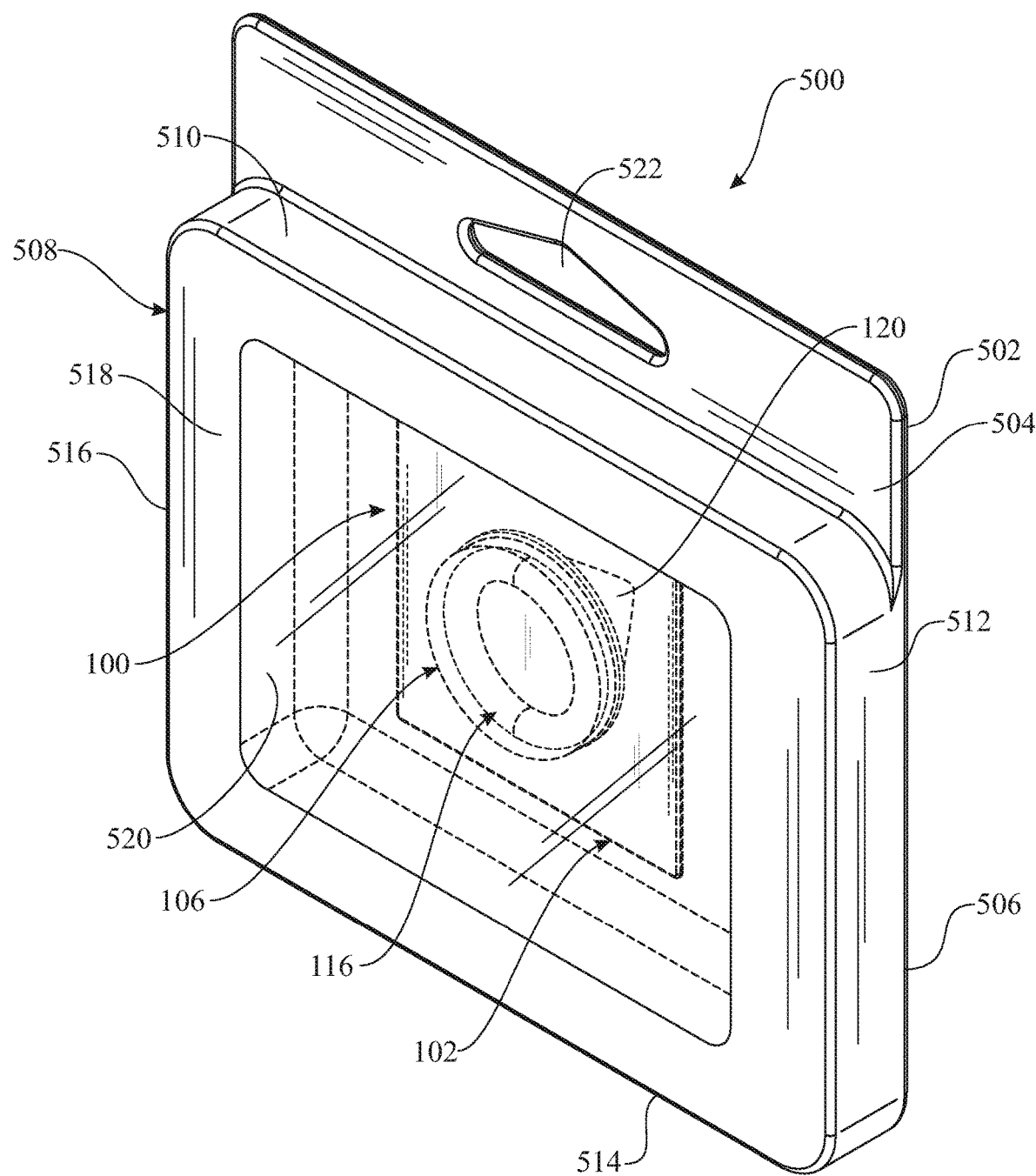
FIG. 8 presents a front perspective view of a cardboard retail package including a transparent window, and a sexual accessory package of FIG. 1 enclosed therein and viewable through the transparent window for readily displaying and selling the sexual accessory package in a retail store.

An alternative retail package 500 is provided in FIG. 8 for packaging and displaying one or more sexual accessory packages 100 for display and sale in retail stores or otherwise. The retail package 500 includes a rigid panel 502 having a front 504 panel, a back panel 506, and a surrounding border 508 having sidewalls 510, 512, 514, 516, a window frame 518, and a transparent window 520 attached to the inner surfaces of the window frame 518. The height of each sidewall 510, 512, 514, 516 defines the size of the storage cavity for packaging one or more sexual accessory packages 100 therein. The transparent window 520 comprises a transparent plastic film that allows purchasers to see through to view the sexual accessory package 100, and physical characteristics of the penile ring 116 through the transparent front panel 108 of the penile ring pack 106. It is understood that the window frame 518 may have different sizes, or shapes to provide a large or small, unobstructed view of the sexual accessory package 100 enclosed within the retail package 500. In one embodiment, at least some portions of a retail package 500 are constructed from a cardboard material to help reduce costs associated with packaging, and to provide environmentally, biodegradable packaging. As with the other retail packages 200, 300, 400, retail package 500 includes a hanger opening 522 for hanging and displaying the sexual accessory package 100 on a rack in retail stores.

It is appreciated that the back panel 208, 308, 408, and 506, of each respective retail package 200, 300, 400, and 500 may include a hinge panel having a series of perforated lines, or tear lines, that permit users to open the hinge panel along the perforated lines to access the one or more sexual accessory packages 100 stored therein. Alternatively, and by way of example, a retail package 500 may include hinged flaps provided anywhere on the surrounding border 508 that can hingedly opened to access the stored one or more sexual accessory packages 100.

Figure 9:
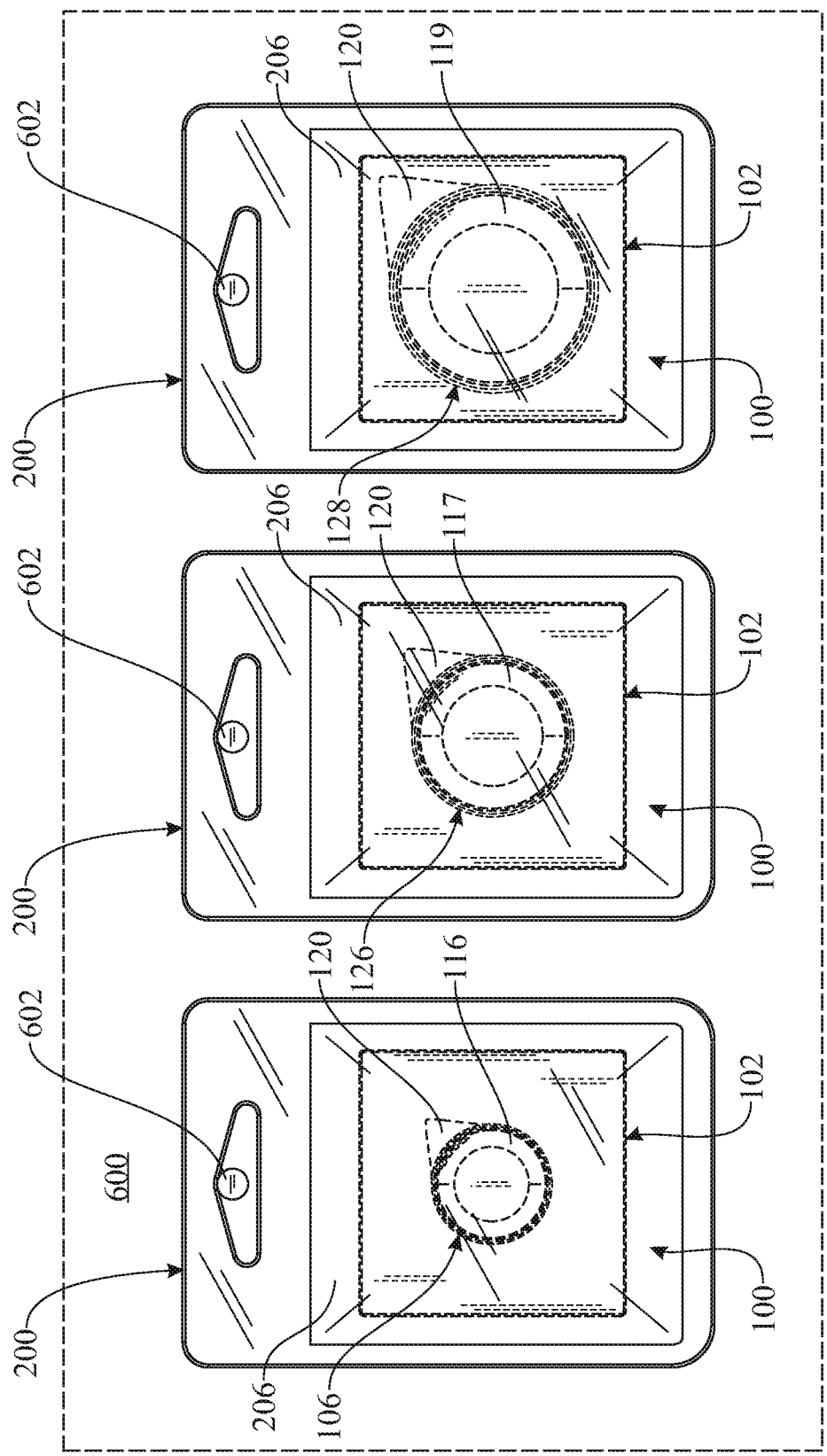
FIG. 9 presents a front view of a plurality of transparent retail packages of FIG. 5 or 6, each including one or more sexual accessory packages having penile rings of different sizes that are accessibly viewable through the transparent retail package, and disposed on one or more display hangers.
Figure 10:
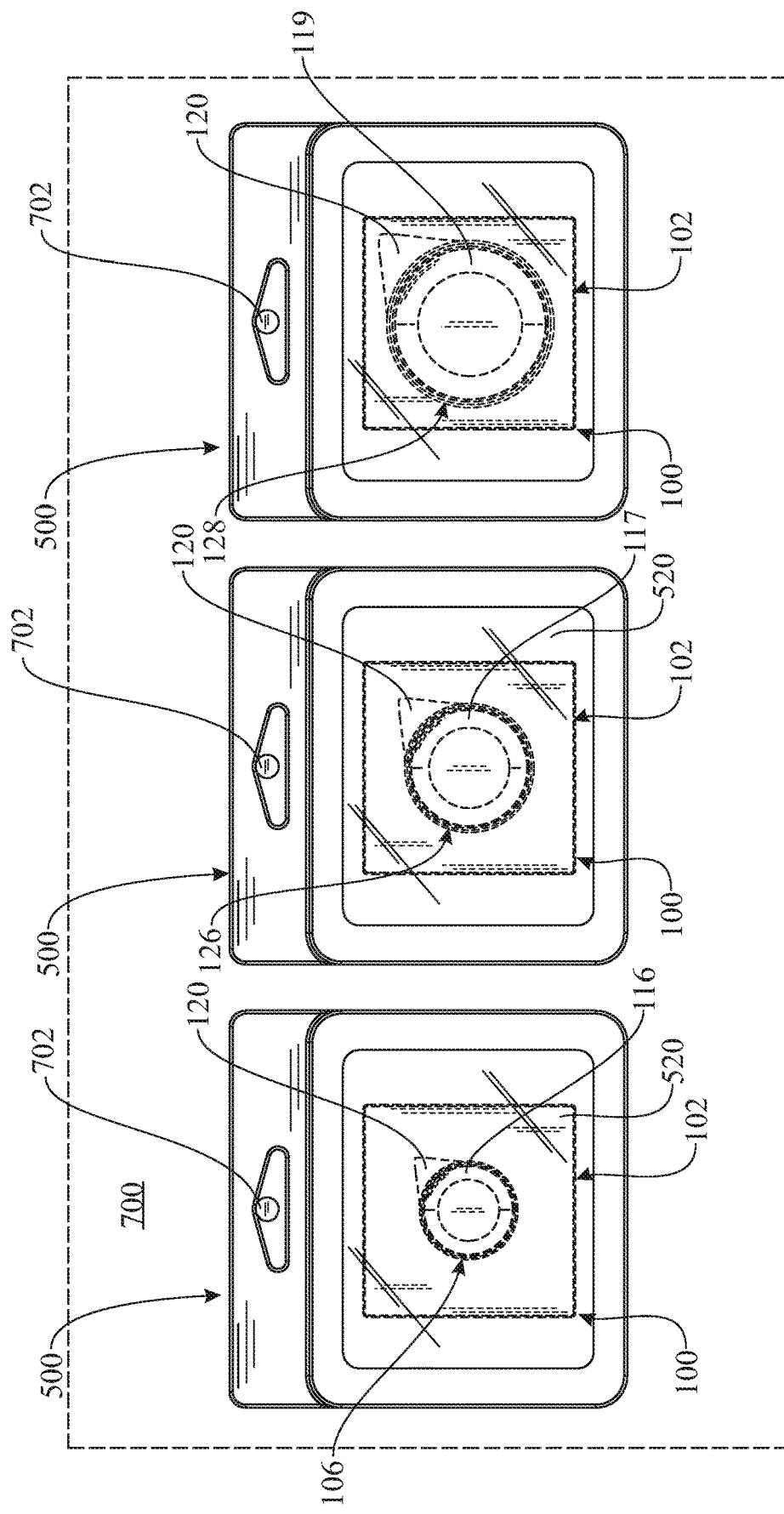
FIG. 10 presents a front view of a plurality of cardboard retail packages of FIG. 8, each including a transparent window, and one or more sexual accessory packages having penile rings of different sizes that are accessibly viewable through the transparent window, and disposed on one or more display hangers.

With reference made to FIGS. 9 and 10, there are shown a front view of a plurality of transparent retail packages 200, 500, respectively, each including one or more sexual accessory packages 100 that are stored on a display rack 600, 700 via hangers 602, 702 for, respectively, display and sale of the sexual accessory packages 200, 500, in retail stores. Both the transparent or translucent retail package 200, and the at least partially transparent or translucent retail package 500, are shown to include penile rings of different sizes such as a small penile ring 116 packaged in a ring package 106 of a first diameter, a medium penile ring 117 packaged in a ring package 126 having a second diameter, and a larger penile ring 119 packaged in a ring pack 128 having a third diameter to accommodate a larger penile ring 119, as may be seen from FIGS. 9 and 10. The transparent or translucent outward extending portion 206 of package 200 and the transparent or translucent window 520 of the retail package 500 both provide for viewing of the penile rings 116, 117, 118 contained therein so that potential buyers may quickly and easily view the style, shape, and size of each penile ring 116, 117, 119 through the transparent of translucent planar front panel 108 of each ring pack 106, 126, 128, and make an informed decision prior to purchase.

As such, the physical construction and layout of the transparent or translucent retail package 200, and the at least partially transparent or translucent retail packages 500 along with the transparent ring packs 106, 126, 128 provide immediate accessible viewing of each penile ring 116, 117, 119 without having to read descriptive contents on packages 200, 500, which some purchasers may be embarrassed or hesitant to do, or without opening the package 200, 500 to view the characteristics of the penile rings 116, 117, and 119, thereby rendering the penile rings 116, 117, and 119 unsellable other than to the purchaser who opened the package. It is understood that such packages 200, 300, 400, and 500 may be situated on any number of racks 600, 700 each having a variety of different configurations. Each retail package 200, 300, 400 and 500 may comprises a generally square or rectangular shape, the same as or similar to, a box, and include a transparent viewing window to allow accessible viewing to packaged penile rings 116, 117, and 119. As such, the retail packages 200, 300, 400, 500 may each comprise any number of different geometrical constructional configurations so long as each provides a transparent or translucent viewing window through at least a portion thereof. Each retail package 200, 300, 400 and 500 may include any color, pattern, design, logo, markings, characters, symbols or other indicia including for example, expiration dates, instructions on use, or description of contents.

Since many modifications, variations, and changes in detail can be made to the described embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A sexual accessory package for display in a retail shopping establishment, said package comprising:
    a condom pack having an outer surface surrounding an inner enclosure, said inner enclosure including a condom removably enclosed therein;
    a penile ring pack including a circular body having a planar front panel integral with a circular wall having an open end disposed opposite said planar front panel, said open end at least partially defined by a perimeter therearound, wherein said planar front panel and said circular wall cooperatively form a ring chamber therebetween;

a penile ring disposed in said ring chamber of said penile ring pack;

a release film overlying said open end of said circular wall opposite said planar front panel and removably attached to at least said perimeter of said circular wall, thereby removably enclosing said penile ring in said ring chamber of said penile ring pack; and said penile ring pack removably attached to said outer surface of said condom pack such that said planar front panel of said penile ring pack is disposed opposite said outer surface of said condom pack for display in the retail shopping establishment to facilitate viewing and sale of said package comprising both said condom and said penile ring.

2. The sexual accessory package as recited in claim 1 wherein at least said planar front panel of said penile ring pack comprises a transparent material of construction such that said penile ring is readily viewable therethrough.

3. The sexual accessory package as recited in claim 1 wherein at least said planar front panel of said penile ring pack comprises a translucent material of construction such that said penile ring is viewable therethrough.

4. The sexual accessory package as recited in claim 1 wherein said planar front panel and said circular wall of said penile ring pack each comprise a transparent material of construction such that said penile ring is readily viewable therethrough.

5. The sexual accessory package as recited in claim 1 wherein said planar front panel and said circular wall of said penile ring pack each comprise a translucent material of construction such that said penile ring is viewable therethrough.

6. The sexual accessory package as recited in claim 1 wherein said circular wall comprises a predetermined height that defines a depth of said ring chamber.

7. The sexual accessory package as recited in claim 6 wherein said depth of said ring chamber is greater than a thickness of said penile ring removably enclosed in said ring chamber.

8. The sexual accessory package as recited in claim 6 wherein said depth of said ring chamber is sufficient to permit a plurality of penile rings to be removably enclosed in said ring chamber one on top of another.

9. The sexual accessory package as recited in claim 1 wherein said penile ring is at least partially defined by a penile ring diameter and said circular wall comprises a diameter that is greater than said penile ring diameter of said penile ring to permit said penile ring to be removably enclosed in said ring chamber.

10. The sexual accessory package as recited in claim 1 wherein said circular wall comprises a diameter that is greater than a diameter of a small penile ring to permit said penile ring to be removably enclosed in said ring chamber.

11. The sexual accessory package as recited in claim 1 wherein said circular wall comprises a diameter that is greater than a diameter of a medium penile ring to permit said penile ring to be removably enclosed in said ring chamber.

12. The sexual accessory package as recited in claim 1 wherein said circular wall comprises a diameter that is greater than a diameter of a large penile ring to permit said penile ring to be removably enclosed in said ring chamber.

13. The sexual accessory package as recited in claim 1 wherein said release film includes a pressure-sensitive adhesive.

14. The sexual accessory package as recited in claim 1 wherein said release film comprises a pull-tab dimensioned and configured to facilitate removal of said release film from said perimeter of said circular wall to permit removal of said penile ring from said ring chamber.

15. The sexual accessory package as recited in claim 1 wherein said release film comprises a pull-tab dimensioned and configured to facilitate removal of said penile ring pack from said outer surface of said condom pack.

16. The sexual accessory package as recited in claim 15 wherein said release film comprises a pull-tab dimensioned and configured to facilitate removal of said release film from said perimeter of said circular wall to permit removal of said penile ring from said ring chamber.

17. The sexual accessory package as recited in claim 14 wherein said pull-tab comprises a triangular configuration.

18. The sexual accessory package as recited in claim 17 wherein said pull ab comprises a stiffener to provide rigidity to facilitate operation of said pull-tab.

19. A sexual accessory package for display in a retail shopping establishment, said package comprising:
    a condom pack having an outer surface surrounding an inner enclosure, said inner enclosure including a condom removably enclosed therein;
    a penile ring pack including a circular body having a planar front panel integral with a circular wall having an open end disposed opposite said planar front panel, said open end at least partially defined by a perimeter therearound, wherein said planar front panel and said circular wall cooperatively form a ring chamber therebetween;
    a penile ring at least partially defined by a penile ring diameter disposed in said ring chamber of said penile ring pack;
    said circular wall comprises a diameter that is greater than said penile ring diameter of said penile ring to permit said penile ring to be removably enclosed in said ring chamber;
    a release film overlying said open end of said circular wall opposite said planar front panel and removably attached to at least said perimeter of said circular wall, thereby removably enclosing said penile ring in said ring chamber of said penile ring pack;
    said planar front panel of said penile ring pack comprises a transparent material of construction such that said penile ring is readily viewable therethrough;
    said release film comprises a pull-tab dimensioned and configured to facilitate removing said release film from said perimeter of said circular wall to permit removal of said penile ring from said ring chamber; and
    said penile ring pack removably attached to said outer surface of said condom pack such that said planar front panel of said penile ring pack is disposed opposite said outer surface of said condom pack for display in the retail shopping establishment to facilitate viewing and sale of said package comprising both said condom and said penile ring.

20. A retail package for containing and displaying at least one sexual accessory package in a retail shopping establishment comprising:
    said at least one sexual accessory package comprising:
        a condom pack having an outer surface surrounding an inner enclosure, said inner enclosure including a condom removably enclosed therein;

a penile ring pack including a circular body having a planar front panel integral with a circular wall having an open end disposed opposite said planar front panel, said open end at least partially defined by a perimeter therearound, wherein said planar front panel and said circular wall cooperatively form a ring chamber therebetween;

a penile ring disposed in said ring chamber of said penile ring pack;

a release film overlying said open end of said circular wall opposite said planar front panel and removably attached to at least said perimeter of said circular wall, thereby removably enclosing said penile ring in said ring chamber of said penile ring pack; and said penile ring pack removably attached to said outer surface of said condom pack such that said planar front panel of said penile ring pack is disposed opposite said outer surface of said condom pack for display in the retail shopping establishment and at least said planar front panel of said penile ring pack comprises a transparent material of construction to facilitate viewing of said at least one sexual accessory package comprising both said condom and said penile ring, and said retail package comprising a rigid panel including a front panel, having an outward extending portion, and a back panel, said front panel and said back panel cooperatively structured to form a storage cavity for containing said at least one sexual accessory package therein, wherein at least one of said outward extending portion or said back panel are constructed from a transparent or translucent plastic material to facilitate viewing and sale of said at least one sexual accessory package comprising both said condom and said penile ring contained therein.

* * * * *